United States Patent
Wecker et al.

(10) Patent No.: US 10,328,181 B2
(45) Date of Patent: Jun. 25, 2019

(54) CERAMIC BONE SUBSTITUTE MATERIAL AND METHOD FOR THE PRODUCTION THEREOF

(71) Applicants: CeramTec GmbH, Plochingen (DE); Friedrich-Alexander-Universität Erlangen-Nürnberg, Erlangen (DE)

(72) Inventors: Heinrich Wecker, Eckental (DE); Alfons Kelnberger, Röthenbach (DE); Peter Greil, Weisendorf (DE); Tobias Fey, Erlangen (DE); Johanna Schmidt, Simmelsdorf (DE); Bodo Zierath, Erlangen (DE)

(73) Assignees: CERAMTEC GMBH, Plochingen (DE); FRIDRICH-ALEXANDER-UNIVERSITÄT ERLANGEN-NÜRNBERG, Erlangen (DE)

( * ) Notice: Subject to any disclaimer, the term of this patent is extended or adjusted under 35 U.S.C. 154(b) by 563 days.

(21) Appl. No.: 14/787,618

(22) PCT Filed: Apr. 28, 2014

(86) PCT No.: PCT/EP2014/058583
§ 371 (c)(1),
(2) Date: Oct. 28, 2015

(87) PCT Pub. No.: WO2014/177509
PCT Pub. Date: Nov. 6, 2014

(65) Prior Publication Data
US 2016/0067381 A1    Mar. 10, 2016

(30) Foreign Application Priority Data

Apr. 30, 2013 (DE) .................. 10 2013 007 401

(51) Int. Cl.
*A61F 2/28* (2006.01)
*A61L 27/10* (2006.01)
(Continued)

(52) U.S. Cl.
CPC .............. *A61L 27/56* (2013.01); *A61F 2/28* (2013.01); *A61F 2/4455* (2013.01); *A61L 27/10* (2013.01);
(Continued)

(58) Field of Classification Search
CPC ........ A61L 27/56; A61L 27/10; A61L 27/105; A61L 2400/08; A61F 2002/30968;
(Continued)

(56) References Cited

U.S. PATENT DOCUMENTS 4,610,832 A * 9/1986 Brockmeyer ...... B01D 39/2093
                                                    210/510.1
5,282,861 A    2/1994 Kaplan
(Continued)

FOREIGN PATENT DOCUMENTS

DE    197 53 249 A1    6/1999
DE    100 15 614 B4    2/2009
(Continued)

OTHER PUBLICATIONS

Brown, et al. "Investigation of Strut Crack Formation in Open Cell Alumina Ceramics", J. Am. Ceram. Soc., 77(6), (1994), pp. 1467-1472.

*Primary Examiner* — Erin Snelting
(74) *Attorney, Agent, or Firm* — Norton Rose Fulbright US LLP

(57) ABSTRACT

A method for producing a ceramic osseoconductive bone substitute material, the bone substitute material, interverte-
(Continued)

bral disk implants containing the substitute bone material, and to methods of using the bone substitute material.

13 Claims, 3 Drawing Sheets

(51) Int. Cl.
  A61L 27/56   (2006.01)
  C04B 35/10   (2006.01)
  C04B 35/64   (2006.01)
  C04B 38/06   (2006.01)
  C04B 35/645  (2006.01)
  A61F 2/44    (2006.01)
  A61F 2/30    (2006.01)

(52) U.S. Cl.
  CPC ............ A61L 27/105 (2013.01); C04B 35/10 (2013.01); C04B 35/64 (2013.01); C04B 35/6455 (2013.01); C04B 38/0615 (2013.01); A61F 2/3094 (2013.01); A61F 2002/30013 (2013.01); A61F 2002/3028 (2013.01); A61F 2002/3092 (2013.01); A61L 2400/08 (2013.01); A61L 2430/02 (2013.01); A61L 2430/38 (2013.01)

(58) Field of Classification Search
  CPC ... A61F 2002/20986; A61F 2002/3092; B01D 39/2093; C04B 38/0615; C04B 35/6455; C04B 38/06; C04B 35/10; C04B 35/101; C04B 35/106
  See application file for complete search history.

(56) References Cited

U.S. PATENT DOCUMENTS

| | | | |
|---|---|---|---|
| 6,547,967 | B1 | 4/2003 | Adler et al. |
| 7,074,479 | B2 | 7/2006 | Rogowski et al. |
| 2005/0228498 | A1 | 10/2005 | Andres |
| 2006/0147332 | A1* | 7/2006 | Jones ................ A61F 2/2803 419/8 |
| 2011/0022180 | A1 | 1/2011 | Melkent et al. |
| 2011/0313538 | A1* | 12/2011 | Oh ..................... A61L 27/56 623/23.61 |

FOREIGN PATENT DOCUMENTS

| | | |
|---|---|---|
| DE | 10 2008 023 911 A1 | 11/2009 |
| EP | 1 329 229 A1 | 7/2003 |

* cited by examiner 2 mm

CERAMIC BONE SUBSTITUTE MATERIAL AND METHOD FOR THE PRODUCTION THEREOF

This application is a § 371 of International Application No. PCT/EP2014/058583 filed Apr. 28, 2014, and claims priority from German Patent Application No. 10 2013 007 401.0 filed Apr. 30, 2013.

FIELD OF THE INVENTION

The invention relates to a method for producing a ceramic bone substitute material and to a ceramic bone substitute material. The invention relates in particular to the production of bone substitute material by way of direct replication, which may be employed as an intervertebral disk replacement.

BACKGROUND OF THE INVENTION

Endoprosthetic components for fusing vertebral bodies are known. They are adapted, in terms of their geometry, to the anatomy of the human vertebral body, are located between two vertebral bodies and completely or partially replace the intervertebral disk During a first phase of their duration in the human body, they typically keep the vertebral bodies at a distance and in an anatomically correct and neurologically optimal position solely by way of their mechanical properties (load-bearing capacity). In the embodiment as a cage, they promote fusion of a bone attached in or on the implant, and thus the adhesion of the two surrounding vertebral bodies in a second phase.

These known components for fusing vertebral bodies are based on metal materials, such as titanium or tantalum, plastic materials such as PEEK, or ceramic materials such as silicon nitride.

Disadvantages of metal materials are, for example:
Metallic abrasion and the resulting negative effects on the human organism, such as foreign body reactions including inflammatory or immunological reactions
Artifacts in imaging for medical diagnostics
Effects of aging and long-term performance (fatigue, corrosion, and the release of metal ions, which can be toxic)

Disadvantages of plastics-based components, such as highly cross-linked PE materials or PEEK, can be as follows:
Insufficient mechanical properties, such as prongs or other elements of the component breaking off, for example during installation. This may adversely affect the human organism.
Lack of presentability in common imaging processes (MRI, X-ray), thereby requiring the use of metallic markers.
Effects of aging and long-term performance, in particular material fatigue.

A fundamental problem that is increasingly becoming the center of attention in implantation operations is the risk of infection during surgery. This risk can be reduced with ceramic components, the surface properties of which may act in an inhibiting manner on bacteria colonization, for example.

Ceramic components based on silicon nitride, for example, are also known.

However, this class of materials was developed with a view toward excellent high-temperature properties—for example for machining of metal components for the automotive industry—and ranks more in the midfield compared to other oxidic system-based ceramic high-performance materials when it comes to the properties required for use as a medical implant, such as strength, hardness and long-term stability.

Moreover, this is a material that is composed of multiple components and comprises needle-shaped silicon nitride particles, embedded into a glass matrix. The sintering of the material is accordingly complex. Mechanical processing, such as grinding or polishing, is thereby likewise extremely demanding and difficult.

All of these disadvantages lead to increased costs in the production of the components, which constitutes a further drawback.

Moreover, components made from $Si_3N_4$ have a rather dark coloration—gray to black—which for purely visual and aesthetic reasons meets with a low level of acceptance in the medical field.

Known ceramic cages generally have an annular design or are adapted to the shape and anatomy of the human vertebral bodies, wherein the ring is composed of a monolithic, which is to say dense, firm and stiff ceramic material.

The center of these cages can have a cavity, which is either filled with (autologous, allogeneic or synthetic) known bone (substitute) materials or has an artificial porous osseoinductive or osseoconductive core structure, which in general is significantly less rigid than the outer ring. In this area, bone cells are intended to form new bone material, wherein the cells involved in this process require an appropriate mechanical stimulus.

A variety of different manufacturing approaches exists with respect to these core structures.

A direct replication technique based on polyurethane foams in combination with a special chemical vapor deposition (CVD) method for depositing tantalum is known from U.S. Pat. No. 5,282,861, for example. The method can be used to produce porous and interconnecting tantalum structures, see FIG. 1, which are to encourage new bone growth. The production process is highly complex, difficult to control and, due in no small part to the tantalum material that is used, also expensive.

What is essential is that interconnecting structures, which is to say open-cell structures, are formed, which contributes to the osseoconductive and osseoinductive nature of the structures produced therewith.

Based on the production process, the individual struts forming the pore-like cavities are composed as follows:

A carbon-containing structure is located at the center, which is created from the polyurethane foam by way of pyrolysis processes and, in the sectional view through the strut, has a triangular shape, see reference numeral 1 in FIG. 2.

Using a CVD method, tantalum is deposited onto these structures, whereby a coating 2 is formed.

The production of osseoconductive structures from ceramic materials is likewise known. One production option is to employ a foaming method in which air is introduced into a ceramic slip, and thus bubbles are created, using specially controlled processes. These structures have relatively high mechanical stability and load-bearing capacity, with compressive strengths in the double-digit megapascal range.

However, it is a disadvantage that no, or almost no, interconnectivity of the porous structures exists, and consequently an essential prerequisite for new bone growth is lacking.

Another variant for forming pores in ceramic structures in a targeted manner is based on the use of organic pore-forming agents, such as organic beads, which are deliberately introduced or applied during the course of the process and then, after burnout, create porosities, see DE 100 15 614 B4, for example.

This technique is suitable for creating rough surfaces. However, it is not suitable for producing components where bone ingrowth is desired since an appropriate interconnectivity of the pores is missing.

OBJECTS OF THE INVENTION

It is therefore the object of the invention to provide a bone substitute material that is made of a bioinert ceramic material, has osseoconductive properties, which is to say comprises interconnective pores, among other things, and can be used as an intervertebral disk implant. This also means that the bone substitute material should have adequate strength, despite high levels of porosity. Furthermore a method is to be provided, which can be used to economically produce such a bone substitute material.

SUMMARY OF THE INVENTION

This object is achieved by the features of the independent method and product claims. The goal is to produce porous ceramic bone substitute materials, which can be used in particular in interbody fusion cages. The bone substitute materials can be composed of oxidic or non-oxidic ceramics. Bone substitute materials made of high-strength $Al_2O_3$ or zirconia toughened alumina (ZTA) ceramics can preferably be used to replace metal or polymer-based cages, for example. However, the use of other ceramic systems, such as SiC, $Si_3N_4$, hydroxylapatite, or the use of composite materials, is likewise conceivable.

DETAILED DESCRIPTION

A method according to the invention for producing bone substitute material that comprises at least one porous ceramic osseoconductive part thus includes at least the following steps:
a) providing a foam or an open-cell foam structure;
b) preparing a ceramic infiltrate suspension;
c) infiltrating the foam with the ceramic infiltrate suspension;
d) debinding the ceramic material and burning out the foam; and
e) sintering.

The bone substitute material according to the invention comprises at least one porous ceramic osseoconductive part, which is characterized by having an open-pore, honeycomb-like cell structure.

An open-pore, honeycomb-like cell structure within the scope of the present invention shall be understood to mean an interconnecting porosity that provides a framework for new bone growth, which is to say acts osseoconductively. Structures that are essentially based on strut-like frameworks made of tantalum, or structures that are based on solid ceramics having a plurality of embedded pores, are known from the prior art. However, the pores of the known ceramic structures are essentially not interconnecting. In contrast, a honeycomb-like structure according to the invention is composed of ceramic struts, which do not impair the patency or the permeability of the pores with respect to body fluids and bone cells. The overall porosity can vary between 50% and 90% and ideally is 65% to 80%. This structure results in an open-cell, which is to say patently connected, pore structure, which allows a microbiological reticulation to be formed, and more particularly enables vascularization of the forming bone substance. This represents a major advantage over closed-cell structures, since in this way the vitality of the formed bone substance is enabled.

Figure 1:
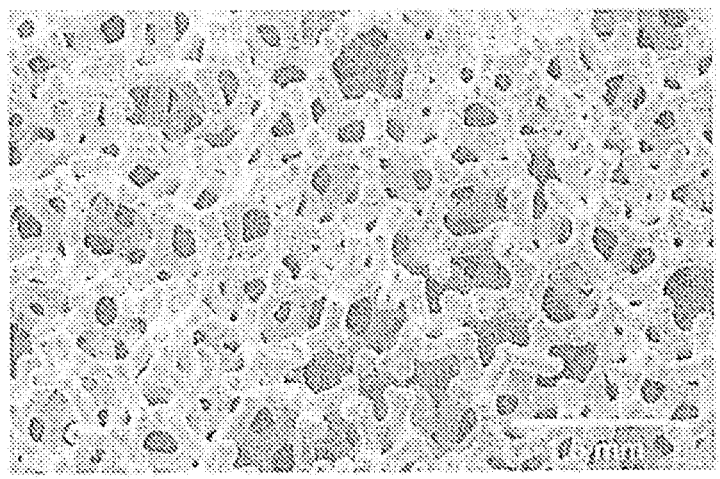
FIG. 1 shows porous tantalum interconnecting structures designed to support new bone formation.
Figure 2:
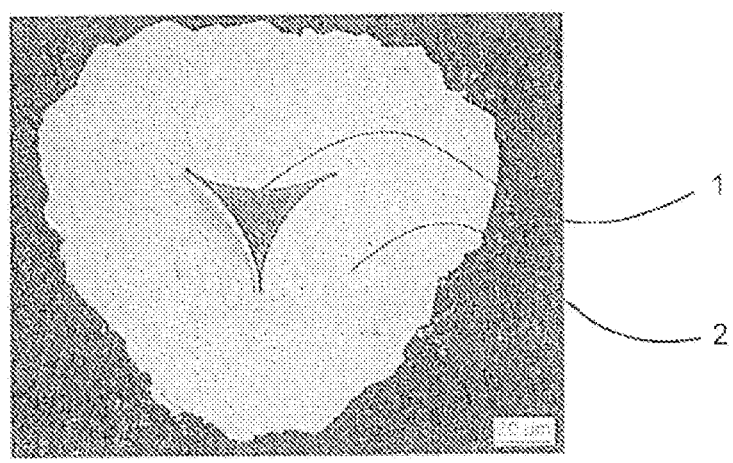
FIG. 2 shows a structure having a carbonaceous structure in the center.
Figure 3:
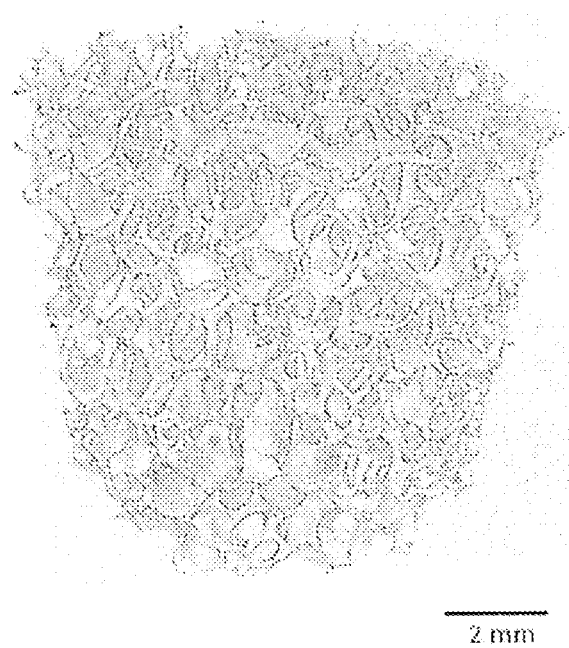
FIG. 3 shows the open pore, honeycomb structure of a bone substitute material prepared with a 45 ppi (pores per inch) polyurethane foam

FIG. 3 shows an X-ray μCT image (microfocus computer tomography) of the open-pore, honeycomb-like structure of a bone substitute material produced by way of a 45 ppi (pores per inch) PU foam as the template carrier.

A particularly preferred method for producing open-cell ceramic foams for bone substitute materials is based on a direct replication technique using a polyurethane template carrier (PU template carrier or PU foams), which is infiltrated or impregnated with a low-viscosity ceramic slip, also referred to as ceramic infiltrate suspension. The ceramic material is preferably $Al_2O_3$-based ceramics or ZTA ceramics.

According to a particularly preferred embodiment of the invention, foams, in particular made of polyurethane, are used as the template carrier. Good results are achieved with foams having a pore density of 30 ppi (pores per inch) to 80 ppi, and preferably 40 to 50 ppi.

A pore density of the foams of 40 to 50 ppi, and more particularly of 45 ppi, has proven to be particularly advantageous, corresponding to an average pore size of 600 μm, since this allows optimal conditions for osseointegration and vascularization to be created.

Figure 4:
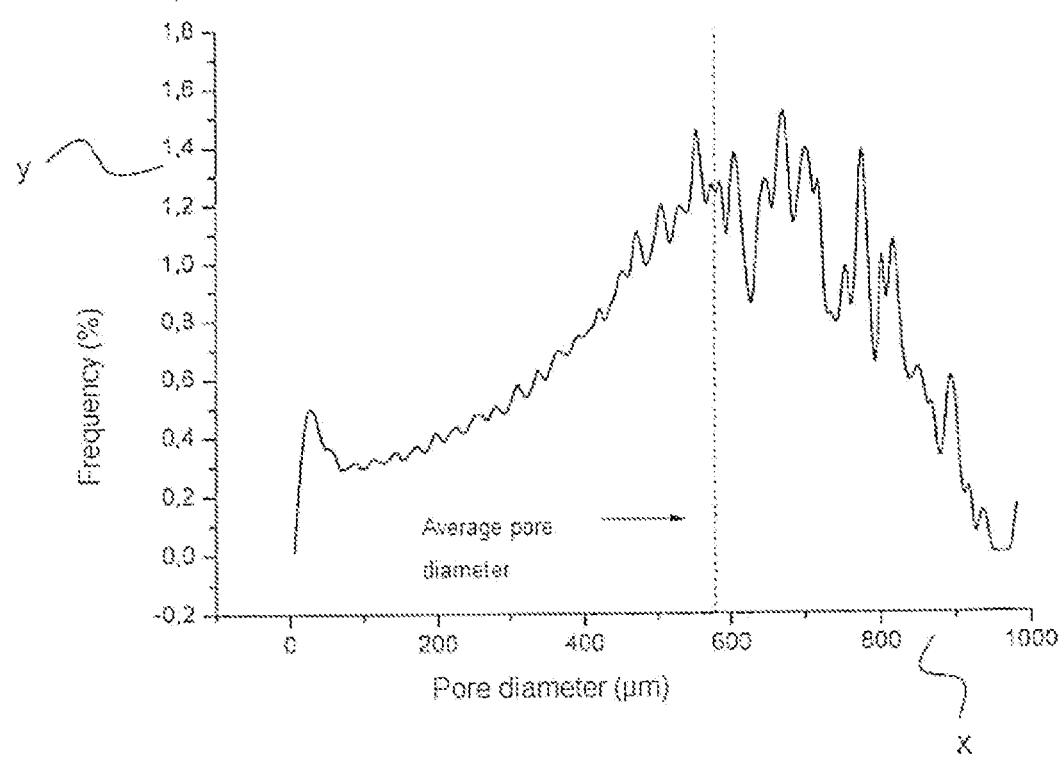
FIG. 4 shows a typical pore size distribution of a bone substitute material according to the invention which was prepared with a 45 ppi polyurethane foam.

In principle, a bone substitute material that was produced by way of the above-mentioned PU foams can advantageously have pore sizes in a range of 200 to 1000 μm, preferably in a range of 400 to 600 μm, and particularly preferably between 300 and 520 μm. FIG. 4 shows a typical pore size distribution of a bone substitute material according to the invention, which was produced by way of a 45 ppi PU foam using the method according to the invention. The pore size is plotted in μm on the x axis against the frequency in % on the y axis.

According to a preferred embodiment of the invention, the pores have an open-cell polyhedral structure, preferably a dodecahedral structure, which results from the pore shape of the PU template carriers.

So as to improve the adhesive power and absorption of the ceramic infiltrate suspension, it may be advantageous to carry out a pre-infiltration of the foams using a primer. For this purpose, a polyvinyl alcohol (PVA) can be used in aqueous systems, for example, and a polyvinyl butyral (PVB) can be used in systems containing organic solvents. Organic suspensions allow higher solids loading at a lower viscosity than aqueous systems. In this way, a higher packing density can be achieved in the coating. Higher sinter densities of the struts allow better mechanical properties to be achieved. Aqueous systems, in contrast, are preferred for environmental reasons.

The preparation and rheological properties of the ceramic infiltration suspension play a very crucial role. Ceramic powder, stabilizers, dispersants, defoamers, and optionally common binding systems are used for this purpose as fundamental components of the suspension.

According to a particularly preferred refinement of the invention, step b), preparing the ceramic infiltration suspension, comprises the following steps:

b.1) blending the fundamental components, and more particularly a solvent, ceramic powder and optional components such as stabilizers, dispersants, defoamers and/or binders; and b.2.) homogenizing and degassing the mixture in an intensive mixer. According to a particularly preferred refinement of the invention, the solvent is water. In principle, all possible organic and inorganic solvents may be used.

As an optional component, according to the invention a mineral acid, such as hydrochloric acid, HCl, is suited and can act as the stabilizer. Hydrochloric acid can also be used as a dispersant, which ensures a homogeneous distribution of the ceramic particles and counteracts agglomeration. Hydrochloric acid, in a content of approximately 7% by volume based on the total volume of the infiltrate suspension, has proven to be particularly advantageous.

Octadecanol can preferably be used as the defoamer, this being an oleic acid, preferably in a content of less than 1% by weight based on the total weight of the infiltrate suspension. So as to avoid the formation of pores during the production of the coated PU foams, the defoamer is used during saturation or infiltration of the foams.

Moreover, common organic binders may be added so as to bind the ceramic particles to the PU template carriers. For example, a PVA- or PVB-based system is suitable for this purpose.

The ceramic infiltrate suspension produced with these components and the ceramic powder is homogenized in an asymmetric mixer between one and 96 hours, or in an intensive mixer for 1 to 10 hours, at room temperature and degassed under a vacuum. Degassing is particularly important for the impregnation of the PU foams so as to prevent the formation of bubbles in the thin struts, and consequently prevent adverse effects on the mechanical properties.

The subsequent infiltration of the PU template carriers with this ceramic infiltrate suspension, this being step c) of the method according to the invention, is carried out in multiple steps between one time and 20 times, wherein the number of steps is dependent on the desired coating thickness.

In principle, the solids loading is dependent on the viscosity of the infiltrate suspension. The viscosity must not exceed the limit value for effective infiltration, which is to say the solids loading should only be high enough to ensure that this limit value is not exceeded. A content between 5 and 50% by volume, based on the volume of the infiltration suspension, has proven to be an advantageous solids loading level of the infiltrate suspension, a value of 20 to 30% being particularly advantageous.

In this way, loading of the PU foam between 20 and 2000% by weight can be achieved, wherein a value between 800 and 1200% by weight, based on the mass of the template carrier foam, has proven to be particularly advantageous. The strut thickness of the foams can be increased by way of loading, whereby the porosity of the finished bone substitute material can be set in a targeted manner.

In the state where the foam is impregnated with the ceramic suspension (green state) or subsequent to a shape-stabilizing annealing operation at a temperature above 800° C. (white state), the surface porosity is optionally at least partially filled or impregnated with a ceramic compound, preferably an $Al_2O_3$-comprising compound having suitable rheological properties for generating a surface suitable for joining or a joining region. This procedure is in particular advantageous when the bone substitute material is to be integrally joined with a further component, such as a cage.

After shaping, the burnout of the PU template carrier is carried out. Complete and non-destructive debinding is required to do so.

This step is preferably carried out at temperatures <600° C. and great caution must be exercised since outgassing of the organic components would otherwise destroy the fragile structures.

Rate-controlled debinding has proven to be particularly advantageous here, in which a debinding rate (material removal per volume and time)<0.1% by weight/($cm^3$ h) should not be exceeded. In particular debinding rates of 0.005 to 0.02% by weight/($cm^3$ h), or <0.02% by weight/($cm^3$ h), have proven to be advantageous. This procedure efficiently allows the destruction of the filigree trabecular, open-cell structures by uncontrolled outgassing of organic components to be avoided.

The time frame for debinding is dependent on the volume of the shaped foam body and is 30 to 50 hours, preferably between 35 and 45 hours, for a body volume of 1 $cm^3$, wherein 1 to 2 g of organic matter is removed per shaped body.

A crucial advantage of the invention also lies in the special thermal treatment of the green, infiltrated template carrier structures, which exhibit increased mechanical stability compared to conventional structures produced based on this method. This will be described in more detail hereafter, wherein the procedure according to the invention results from the following dilemma.

Figure 5A:
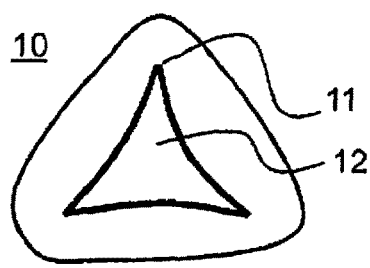
FIGS. 5a and 5b show hollow webs with the triangle-shaped cross section.
Figure 5B:
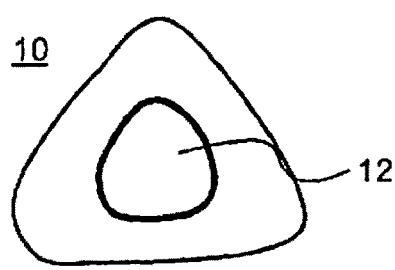

Replication and subsequent burnout of the PU foam causes cavities—known as hollow struts—having a triangular shape to be formed in the individual struts that span the honeycomb-shaped or trabecular structure. FIGS. 5a and 5b show these hollow struts 10 having the triangular cross-section. As is apparent from FIG. 5a, the hollow struts 10 have pointed ends 11 in the cross-sectional view. The cavities 12 as such generally negatively impact the mechanical load-bearing capacity of the trabecular structure. Cracks and material failure tend to originate from the pointed ends 11.

Figure 5C:
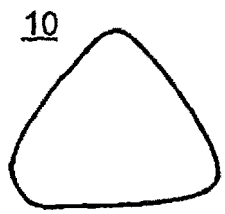
FIG. 5c shows an embodiment with the hollow member eliminated.

Based on this, it was derived that the pointed ends, from which cracks and material failure can originate, can be optimized by adapting the geometry, such as by reducing the curvature at the notch base by way of rounding, see FIG. 5b, or by completely eliminating the hollow struts, see FIG. 5c, so as to increase the mechanical stability.

According to the invention, the solution to this problem provides for subjecting the debindered structures to a multi-stage sintering process, during which the hollow struts are rounded and at least partially eliminated.

As a result, a multi-stage sintering process e) is preferred, comprising the following steps:

e.1) prefiring the structures at temperatures of up to 1400 to 1500° C.; and e.2) hot isostatic pressing (HIP) in a high-pressure inert gas atmosphere, and more particularly an argon atmosphere, at a pressure of up to 1400 bar and a temperature of up to 1500° C. over a time period of up to 60 hours.

Based on a known replication method, this procedure according to the invention yields the following new and inventive advantages.

The porosity in the hollow struts is minimized, whereby the strength of the bone substitute material is increased. At the same time, the multi-stage sintering process, and more particularly the HIP process, optimizes the geometry of the hollow struts with respect to the tips so that the strength is increased further. Pores still present agglomerate at the formerly pointed ends of the hollow struts. Thus, the pointed ends are precisely avoided which otherwise would have represented a weak point in the ceramic structure.

The mechanical strength of the structures thus generated can consequently be decisively increased. Typical compressive strengths of the bone substitute material range from 2 to 20 MPa, with preferred compressive strengths ranging from 15 to 20 MPa.

The bone substitute material can be coated, or at least partially filled, with osseoinductive materials, such as tricalcium phosphate or hydroxylapatite, or also with organic osseoinductive compounds.

A component made of bone substitute material can be used for such a purpose. However, according to a preferred embodiment of the invention, the bone substitute material can also be part of a prosthesis, and more particular of an endoprosthesis.

The bone substitute material can accordingly also be part of an intervertebral disk implant or be used as an intervertebral disk implant. A preferred embodiment of an intervertebral disk implant comprises at least one load-bearing part and at least one porous ceramic osseoconductive part. The osseoconductive part is preferably composed of an above-described ceramic bone substitute material. The load-bearing part preferably comprises a dense, substantially non-porous ceramic material, the porosity of which is preferably less than 5%, particularly preferably less than 2%, and most particularly preferably less than 0.5%.

According to one embodiment of the invention, the load-bearing part and the osseoconductive part can be integrally bonded by way of joint sintering.

According to a further embodiment, the load-bearing part and the osseoconductive part can also form a modular system, which can be individually compiled. According to a particularly preferred embodiment, the modular system can be positively joined by way of a plug connection.

Based on a predefined model geometry, initially an osseoconductive part can be produced from bone substitute material, which can then be inserted into a separately produced, finished sintered load-bearing part and positively joined thereto.

This has the advantage that it is possible to generate combinations of the core and shell structures which are tailored to the patient even while conducting the surgical procedure, and a high degree of flexibility is ensured.

Merely positive joining, which is to say no joining by way of bonding, clamping, sintering or in another manner, moreover has the advantage that the introduction of biomechanical forces into the shell structure (load-bearing part) and the core structure (osseoconductive part) of the cage are decoupled from each other, whereby the micromechanical stimulation of bone growth in the region of the core structure can be favorably influenced independently from the firm and very rigid shell structure.

After sintering of the osseoconductive part, a surface treatment is optionally carried out to set the exact geometry and tolerances so as to achieve an optimal joining fit with the load-bearing part in the modular design.

A step in the shell region can be used to fix the position of the core structures (osseoconductive part).

An intervertebral disk implant according to the invention can, of course, also be made available in an integrated construction. The load-bearing and osseoconductive parts are then manufactured by separate production in the green state and subsequent joint sintering, resulting in integral joining.

Figure 6:
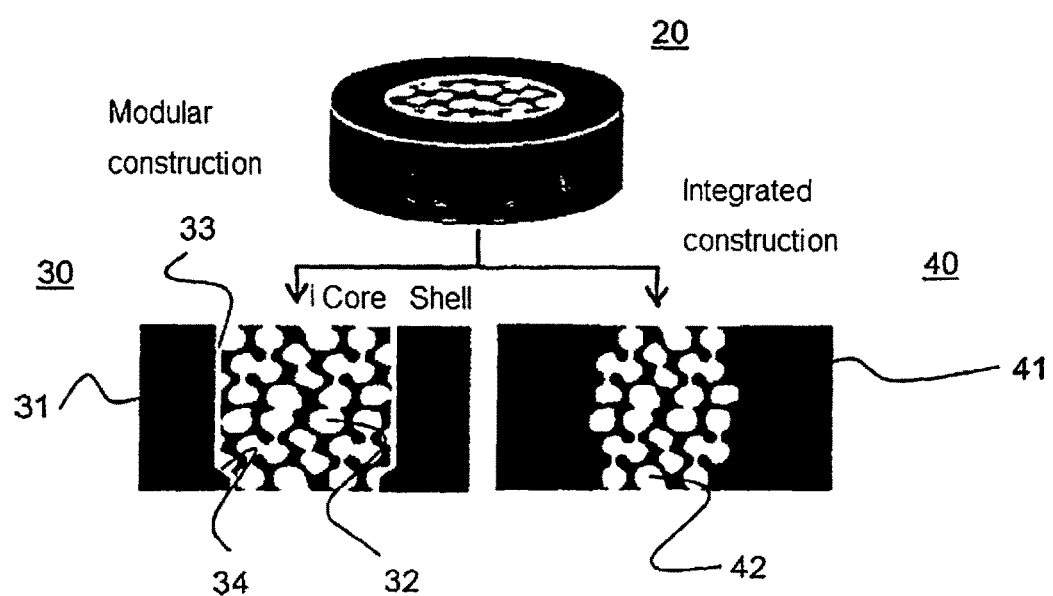
FIG. 6 shows an example of essential distinctive features of the modular and integrated embodiments of intervertebral implants.

FIG. 6 shows essential distinguishing features of modular and integrated embodiments of intervertebral disk implants 20 by way of example. The implant 30 has a modular construction, which is apparent from the joining gap 33, provided in a clearly visible manner merely for illustration purposes, between the load-bearing part 31 and the osseoconductive part 32. Moreover, a projection 34 in the load-bearing part 31 is apparent in the lower region of the implant. The shape of the osseoconductive part 32 can be adapted to this projection 34 in a variety of ways. In FIG. 4, the osseoconductive part 32 has a projection that is complementary to the projection of the load-bearing part 34. Other, merely form-locked alternatives are known to a person skilled in the art and shall, of course, not be excluded by this example.

The integrated construction is shown by way of example based on the intervertebral disk implant 40. The load-bearing part 41 and the osseoinductive part 42 were joined in the green state and subsequently jointly sintered. This results in an integral joint between the two parts 41 and 42.

With respect to the integrated construction, it is generally important that the shrinkage behaviors of the osseoconductive part and the load-bearing part are approximately similar, since this is the only way to prevent detachment and a gap opening between the shell and core areas. In addition, this is the only way to ensure optimal sintered bonding of the two structures.

To ensure an optimal sintered bond or integral joint, it has proven to be advantageous when the infiltrated foam is approximately 2 to 20% larger than the diameter provided in the green load-bearing part. After joining, the infiltrated foam is under pressure, ensuring direct contact with the load-bearing part. In this way, the necessary exchange of substances with the load-bearing part is promoted during sintering.

The invention claimed is:

1. A method for producing a bone substitute material, including at least one porous ceramic osseoconductive part, comprising the steps of:
   a) providing a foam having a pore density of 30 to 80 ppi;
   b) preparing a ceramic infiltrate suspension that contains a ceramic material selected from the group consisting of an $Al_2O_3$-based ceramic material and a ZTA ceramic material;
   c) infiltrating the foam with the ceramic infiltrate suspension;
   d) debinding the ceramic material and burning out the foam; and
   e) sintering; wherein the sintering comprises the steps of prefiring at a temperature in the range of 1400 to 1500° C., and hot isostatic pressing in an inert gas atmosphere at less than or equal to 1400 bar and a temperature of less than or equal to 1500° C.

2. The method according to claim 1, wherein the foam is open-pore foam.

3. The method according to claim 1, wherein the foam has a pore density of from 40 to 50 ppi.

4. The method according to claim 1, wherein step b), preparing the ceramic infiltrate suspension, comprises the following steps:
   b.1) blending a solvent and the ceramic material to form a mixture;
   b.2) homogenizing and degassing the mixture in an asymmetric mixer and/or an intensive mixer to form the infiltrate suspension, said infiltrate suspension having a rheology; and
   b.3) setting the rheology of the infiltrate suspension.

5. The method according to claim 4, wherein the solvent is water.

6. The method according to claim 4, wherein in step b.2) the homogenizing and the degassing the mixture in an asymmetric mixer and/or an intensive mixer is performed under vacuum.

7. The method according to claim 6, wherein in step b.2) the homogenizing and the degassing the mixture in performed in the asymmetric mixer.

8. The method according to claim 4, wherein in step b.2) the homogenizing and the degassing the mixture in performed in the asymmetric mixer.

9. The method according to claim 1, wherein a solids loading of the infiltrate suspension is between 5 and 50% by volume, based on the volume of the suspension.

10. The method according to claim 1, wherein a surface porosity is entirely or partially filled with a ceramic compound, whereby a joining region for joining to another component is obtained.

11. The method according to claim 10, wherein the ceramic compound comprises $Al_2O_3$.

12. The method according to claim 1, wherein method step d), debinding and burning out, is carried out at temperatures of less than 600° C. and a debinding rate of <0.1% by weight/($cm^3$ h).

13. The method according to claim 1, wherein the ceramic material comprises the $Al_2O_3$-based ceramic material.

* * * * *